United States Patent [19]

aus der Fünten et al.

[11] 4,113,741
[45] Sep. 12, 1978

[54] METHOD OF PREPARING PHTHALIDE

[75] Inventors: Helmut aus der Fünten, Niederkassel; Wilhelm Vogt, Cologne, both of Germany

[73] Assignee: Dynamit Nobel Aktiengesellschaft, Cologne, Germany

[21] Appl. No.: 783,576

[22] Filed: Apr. 1, 1977

[30] Foreign Application Priority Data

Apr. 15, 1976 [DE] Fed. Rep. of Germany ....... 2616741

[51] Int. Cl.$^2$ .......................................... C07D 307/88
[52] U.S. Cl. ............................................. 260/343.3 R
[58] Field of Search ................................. 260/343.3 R

[56] References Cited

U.S. PATENT DOCUMENTS 2,114,696  3/1935  Austin et al. ................. 260/343.3 R Primary Examiner—Natalie Trousof
Assistant Examiner—Jane T. Fan
Attorney, Agent, or Firm—Burgess, Dinklage & Sprung

[57] ABSTRACT

Method for preparing phthalide by the catalytic dehalogenation of 3-chlorophthalide in the presence of hydrogenation catalyst and in the presence of an HCl acceptor.

The phathalide which is produced is a valuable chemical intermediate for the manufacture of dyes, plant protecting agents and pharmaceuticals.

8 Claims, No Drawings

METHOD OF PREPARING PHTHALIDE

BACKGROUND

The invention relates to a method of preparing phthalide by the catalytic dehalogenation of 3-chlorophthalide in the presence of HCl acceptors.

Numerous processes are described in the literature for the preparation of phthalide by reactions of o-disubstituted benzenes, such as phthalic acid dichloride, o-xylyl chloride, o-tolylic acid, o-phthalic aldehyde, o-xylylene glycol, phthalimide and the like. Phthalide is formed from these starting substances only after a plurality of difficult process steps or in an unsatisfactory yield. Other methods of preparing phthalide are the reductions of phthalic acid anhydride, which are performed, for example, with zinc and glacial acetic acid (Ber. 17, 2178 [1884]), by catalytic hydrogenation with noble metal catalysts (F. Zymalkowski, "Katalytische Hydrierung im Organisch-Chemischen Laboratorium," Ferd. Enke Verlag Stuttgart, 1965, page 186), or in the presence of nickel (German Reich Pat. No. 368,414).

In these reductions of phthalic acid anhydride to phthalide, reaction water forms, which leads to trouble in the course of the hydrogenation and results in contaminated products. These disadvantages are partially overcome in the electrochemical reduction of phthalic acid anhydride (Bull. Chem. Soc. Japan 7, 127 [1932], German Offenlegungsschrift No. 2,144,419), yet the performance of electrochemical processes generally presents technical difficulties and involves a relatively great investment in apparatus.

THE INVENTION

It has been found that phthalide can be prepared in surprisingly good yields and free of by-products in a simple manner by the dehalogenation of 3-chlorphthalide in the presence of HCl acceptors.

The reaction takes place in accordance with the equation:

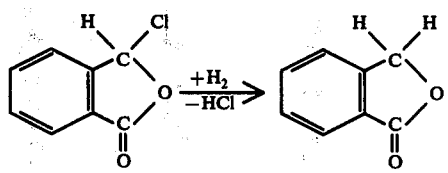

The dehydrohalogenation of 3-chlorophthalide can be performed, for example, by the reaction of 3-chlorophthalide, in substance or dissolved in an inert organic solvent, in the presence of catalysts and HCl acceptors at a slight hydrogen excess pressure, thus forming phthalide.

The process of the invention is not limited to a specific type of catalyst.

Usable are noble metal catalysts and especially hydrogenation catalysts of the 8th Group of the Periodic Table of the Elements. Preferred catalysts are palladium and nickel. The catalyst can be used plain or precipitated on a support. Suitable supporting substances are carbon, aluminum oxide, silicon dioxide, barium sulfate, bentonite, diatomaceous earth and kieselgur. The catalyst is used in an amount of about 0.1 to about 15%, preferably about 0.1 to about 8%, of the weight of the 3-chlorophthalide.

The reaction of 3-chlorophthalide takes place at a high speed between about $-10°$ and about $150°$ C., at pressures of about 0.2 to about 100 bars. The preferred range is at temperatures of about $10°$ to about $70°$ C. and at pressures of about 1 to 20 bars.

Aliphatic, cycloaliphatic and aromatic hydrocarbons can, for example, be used as solvents, but so can ethers such as diethyl ether, dimethoxyethane, tetrahydrofuran and dioxane, organic carboxylic acids such as formic acid, acetic acid, propionic acid and their esters, and tertiary aliphatic or aromatic amines.

For the neutralization of the hydrochloric acid that forms in the reaction, HCl acceptors are used in at least stoichiometric quantity. Suitable for this purpose are for instance, not only tertiary amines, such as triethylamine and N-dimethylaniline, but also inorganic compounds such as sodium carbonate, sodium bicorbonate, sodium formate and sodium acetate. Instead of the above-named sodium compounds, the corresponding potassium (or other alkali metal) salts or the salts of the alkaline earth metals can also be used with equal success.

The isolation of phthalide can be performed after the reaction has ended by separating the catalyst together with the salt that has formed. The catalyst can be reused for additional dehalogenations after the salt has been washed out of it. After distilling out the solvent, phthalide is then obtained by simple vacuum distillation, in purities of up to 99.35% (gas-chromatographic analysis).

The phthalide prepared by the method of the invention is a valuable chemical intermediate for the manufacture of dyes, plant protecting agents and pharmaceuticals.

The phthalide which is produced is a valuable chemical intermediate for the manufacture of dyes, (e.g. derivates of anthrachinone) or 3-bromo phthalide, which is used to introduce the phthalidyl-group in antibiotics (e.g. U.S. Pat. Nos. 3,860,579; 3,919,196; 3,939,180; 3,963,792 and 3,963,704). Furthermore phthalide is used as a plasticizer for nitrocellulose.

EXAMPLES

The following examples will serve to explain the invention:

Example 1

A 1-liter lift magnet autoclave is charged with 110 g of 3-chlorophthalide, 10 g of nickel catalyst RCH 55/10 (commercial product of Farbwerke Hoechst AG) and 400 ml of tetrahydrofuran to which 66 g of triethylamine is added. After purging the air with nitrogen, hydrogen is pumped in to a pressure of 10 bars, and the temperature is raised, with stirring, to $65°$ C. The hydrogen consumption is compensated by additions in the range between 10 and 20 bars for a period of $4\frac{1}{2}$ hours. After the absorption of hydrogen ceases, the catalyst and precipitated salt are filtered out and the solvent is withdrawn. After distillation of the residue between $88°$ and $90°$ C. and 0.2 Torr, 77.5 g of phthalide is obtained, of a melting point of $71°$ C. (gas-chromatographic analysis 98.95%).

Yield: 89% of the theory.

Example 2

As described in Example 1, an autoclave is charged with 110 g of 3-chlorophthalide, 5 g of palladium-on-charcoal catalyst (metal content 5%), 54 g of sodium acetate and 400 ml of glacial acetic acid, and treated for 1.5 h with hydrogen at 5 to 10 bars of pressure and $20°$ to 35° C. After filtration and working up by distillation, 76.5 g of phthalide is obtained, melting point 72°–73° C. (gas-chromatographic analysis 99.35).

Example 3

The catalyst filtered off in Example 2 is washed three times with 20 ml of warm water and 10 ml of acetic acid each time. With the use of this catalyst and the amounts and conditions specified in Example 2, 75.9 g of phthalide are obtained having the same purity as in Example 2.

What is claimed is:

1. Method of preparing phthalide which comprises reacting 3-chlorophthalide with hydrogen at a pressure of about 0.2 to about 100 bars in the presence of a hydrogenation catalyst and in the presence of an HCl acceptor.
2. Method of claim 1 wherein the pressure is about 1 to about 20 bars.
3. Method of claim 1 wherein the reaction is performed at about −10° to about 150° C.
4. Method of claim 3 wherein the reaction is performed at about 10° to about 70° C.
5. Method of claim 1 wherein the hydrogenation catalyst is a metal of the 8th Sub-Group of the Periodic System.
6. Method of claim 5 wherein the pressure is about 1 to about 20 bars.
7. Method of claim 5 wherein the reaction is performed at about −10° to about 150° C.
8. Method of claim 7 wherein the reaction is performed at about 10° to about 70° C.

* * * * *